United States Patent [19]

Hubble, III et al.

[11] Patent Number: 4,553,033

[45] Date of Patent: Nov. 12, 1985

[54] INFRARED REFLECTANCE DENSITOMETER

[75] Inventors: Fred F. Hubble, III, Rochester; James P. Martin, Dansville, both of N.Y.

[73] Assignee: Xerox Corporation, Stamford, Conn.

[21] Appl. No.: 525,849

[22] Filed: Aug. 24, 1983

[51] Int. Cl.⁴ .................. G01N 21/47; G03G 15/08
[52] U.S. Cl. .................... 250/353; 250/341; 355/14 D; 356/445
[58] Field of Search ............. 250/341, 353, 354.1, 250/358.1, 359.1, 360.1; 356/445, 448; 355/14 D

[56] References Cited

U.S. PATENT DOCUMENTS

| | | | |
|---|---|---|---|
| 3,659,556 | 5/1972 | Mutschler | 118/637 |
| 3,712,203 | 1/1973 | Kishi et al. | 95/89 R |
| 3,756,192 | 9/1973 | Locklar et al. | 118/7 |
| 3,830,401 | 8/1974 | Benwood et al. | 222/57 |
| 3,854,050 | 12/1974 | Peterson et al. | 250/461.2 |
| 4,146,325 | 3/1979 | Lange | 355/14 D |
| 4,207,467 | 6/1980 | Doyle | 250/341 |
| 4,457,615 | 7/1984 | Seanor | 355/15 |
| 4,458,152 | 7/1984 | Bonora | 250/353 |

FOREIGN PATENT DOCUMENTS

| | | | |
|---|---|---|---|
| 51646 | 5/1981 | Japan | 356/445 |
| 70442 | 6/1981 | Japan | 356/448 |

OTHER PUBLICATIONS

Troy et al., "Reducing Stray Light Errors in the Hunter Multipurpose Reflectometer", J. Opt. Soc. Am., 40 (2), Feb. 1950, pp. 80–82.

*Primary Examiner*—Alfred E. Smith
*Assistant Examiner*—Carolyn E. Fields
*Attorney, Agent, or Firm*—Ronald F. Chapuran

[57] ABSTRACT

An integral, compact infrared reflectance densitometer including a substrate supporting an LED, a control photodiode to compensate for component degradation, a background photodiode to compensate for background radiation, and a large area photodiode to provide an electrical signal representative of the amount of toner particles on the photosensitive surface. Also carried on the substrate is a field lens to focus light rays reflected from the photosensitive surface onto the signal photodiode. The substrate is precisely secured to a molded housing having integral collector and collimating lenses. Four extending pins on the housing engage four apertures on the substrate to locate the substrate with respect to the housing and align the LED and field lens carried on the substrate with the collector and collimating lenses of the housing. Also carried on the substrate is an aperture box to permit a portion of the LED light to project through the collimating lens to the photosensitive surface and a portion of the light to be reflected onto the control photodiode to control light output. The light rays reflected from the photosensitive surface are gathered in a collector lens and projected through the field lens to be focused onto the signal photodiode. An L-shaped clip and an appendage with an elongated aperture extend from opposite ends of the housing to position and align the infrared reflectance densitometer in the reproduction machine with respect to the photosensitive surface.

11 Claims, 7 Drawing Figures

INFRARED REFLECTANCE DENSITOMETER

This invention relates to densitometers, and more particularly to a reflectance densitometer for measuring and controlling the density of particles on a reflective surface.

The use of infrared reflectance densitometers is well known, particularly in electrostatic imaging in which electroscopic toner particles are applied imagewise to a photoconductive surface and then transferred to a support surface such as paper to be permanently fixed. In order to provide the necessary quality control during this process, it is desirable to monitor and control the amount of toner deposited on the photoconductive surface prior to its transfer to the copy sheet.

The prior art is replete with devices to monitor and control the application of toner to a photosensitive surface. U.S. Pat. No. 3,659,556 teaches the use of light reflected from a developed image on the photoreceptor to determine the optical density of that image. In particular, a lamp directs light toward the photoreceptor and a photocell receives the reflected light to determine the density of the developed image on the photoreceptor. In response to the signal generated by the photocell, suitable circuitry drives a motor to dispense toner into the development housing.

U.S. Pat. No. 3,712,203 discusses the use of a light source sensed by a pair of photoelectric cells, one of the cells sensing through a filter giving a standard toner concentration reference. Based on the difference in the intensities of the light sensed, the opening of a toner supply valve is controlled to maintain the toner concentration within the developer constant.

U.S. Pat. No. 3,756,192 teaches a toner concentration control system for a copier in which light is alternately reflected from multicomponent developer material containing toner and from a calibrated reflector to a photosensor. An imbalance of toner in the developer material results in a difference in reflected light intensity from the developer and reflector that is converted into an electrical signal to control a toner replenishing device.

U.S. Pat. No. 3,830,401 discloses a source of radiant energy reflected from the developer mixture and monitored by a photoelectric transducer to produce a first output signal representative of the intensity of the reflectance. A second photoelectric transducer directly illuminated by the source produces a second output signal representative of the intensity of the radiation emanating from the source as modulated by the surrounding environment. Pending application U.S. Ser. No. 198,993 filed Oct. 21, 1980 teaches the use of a toner concentration sensor having a collimated light beam to compensate for changes in distance from a photoreceptor.

A difficulty with the prior art devices is that they are generally relatively large, complex and expensive and subject to component degradation and background interference. In addition, if the photosensitive surface is a photoreceptor web, not only the translation but also the rotation of the web during operation can often inhibit accurate measurements of toner concentration on the web. It is, therefore, an object of the present invention to provide a relatively inexpensive and compact infrared reflectance densitometer that is relatively easy to mount and align in a reproduction machine. It is another object of the present invention to provide a densitometer that not only compensates for component degradation but also eliminates interference from background light in providing accurate measurements. It is still another object of the present invention to provide a densitometer that gives uniform and accurate measurements of the optical density of toner on the photosensitive surface independent of not only the translation of the photosensitive surface but also the rotation of the web during measurement. It is another object of the present invention to provide an infrared reflectance densitometer that is a compact unit having both optical and electrical capabilities and including alignment and mounting devices integral with the compact unit. Further objects and advantages of the present invention will become apparent as the following description proceeds and the features of novelty characterizing the invention will be pointed out with particularity in the claims annexed to and forming a part of this specification.

Briefly, the present invention is concerned with an integral, compact infrared reflectance densitometer including a substrate supporting an LED, a control photodiode to compensate for component degradation, a background photodiode to eliminate background radiation, a signal photodiode to provide an electrical signal representative of the amount of toner particles on the photosensitive surface, and an integrated circuit chip to perform LED drive and signal processing functions. Also carried on the substrate is a field lens to focus light rays reflected from the photosensitive surface onto the signal photodiode. The substrate is secured to a molded housing having integral collector and collimating lenses. Four extending pins on the housing engage four apertures on the substrate to locate the substrate with respect to the housing and align the LED and field lens carried on the substrate with the collector and collimating lenses of the housing and to secure the substrate by mechanical interference between the pins and substrate. Also carried on the substrate is an aperture box to permit a portion of the LED light to project through the collimating lens to the photosensitive surface and a portion of the light to be reflected onto the control photodiode to control light output. The light rays reflected from the photosensitive surface are gathered in a collector lens and projected onto the field lens to be focused onto the signal photodiode. An L-shaped clip and an appendage with an elongated aperture extend from opposite ends of the housing to position and align the infrared reflectance densitometer in the reproduction machine with respect to the photosensitive surface.

For a better understanding of the present invention, reference is made to the accompanying drawings wherein the same reference numerals have been applied to like parts and wherein.

Figure 1:
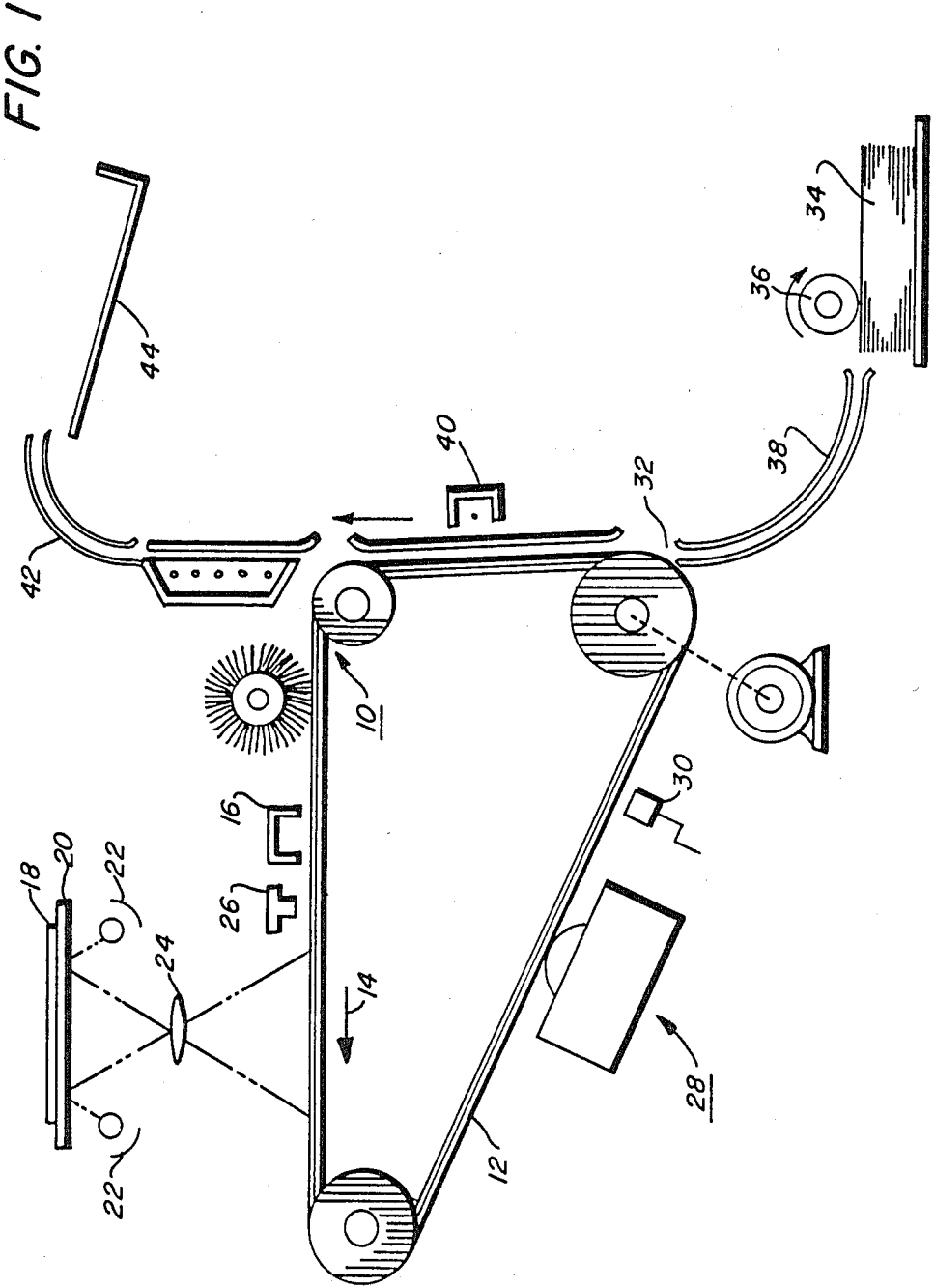
FIG. 1 is a schematic elevational view of an electrophotographic printing machine incorporating the features of the present invention.

With reference to FIG. 1, there is illustrated an electrophotographic printing maching have a belt 10 with a photoconductive surface 12 moving in the direction of arrow 14 to advance the photoconductive surface 12 sequentially through various processing stations. At a charging station, a corona generating device 16 electrically connected to a high voltage power supply charges the photoconductive surface 12 to a relatively high substantially uniform potential. Next, the charged portion of the photoconductive surface 12 is advanced through an exposure station. At the exposure station, an original document 18 is positioned upon a transparent platen 20. Lamps 22 illuminate the original document and the light rays reflected from the original document 18 are transmitted through lens 24 onto photoconductive surface 12. The exposure station preferably also includes test area generator 26 comprising a light source providing a test light image projected onto the photoconductive surface 12 to record a test area. The test area will be developed with toner particles at a development station.

A magnetic brush development system illustrated at 28 advances a developer material into contact with the electrostatic latent image in the test area at the development station. The developed test area passes beneath an infrared densitometer or toner sensor 30. The infrared densitometer 30 is positioned adjacent the photoconductor surface 12 near the developer station to generate electrical signals proportional to the developer toner mass of the test area.

At the transfer station 32, a sheet of support material in tray 34 is moved into contact with the toner powder image. The sheet of support material is advanced to the transfer station 32 by sheet feeding apparatus, preferably including a feed roll 36 contacting the uppermost sheet in tray 34. Feed roll 36 rotates so as to advance the uppermost sheet from tray 34 into chute 38. The chute 38 directs the advancing sheet of support material into contact with the photoconductive surface 12 in timed sequence in order that the toner powder image developed thereon contacts the advancing sheet of support material at the transfer station.

After transfer, the sheet continues to move into a conveyor which advances the sheet to a fuser assembly 40 for permanently affixing the transferred powder image to the sheets of support material. After fusing, the chute 42 drives the advancing sheet to catch tray 44 for removal from the printing machine by the operator.

Figure 2:
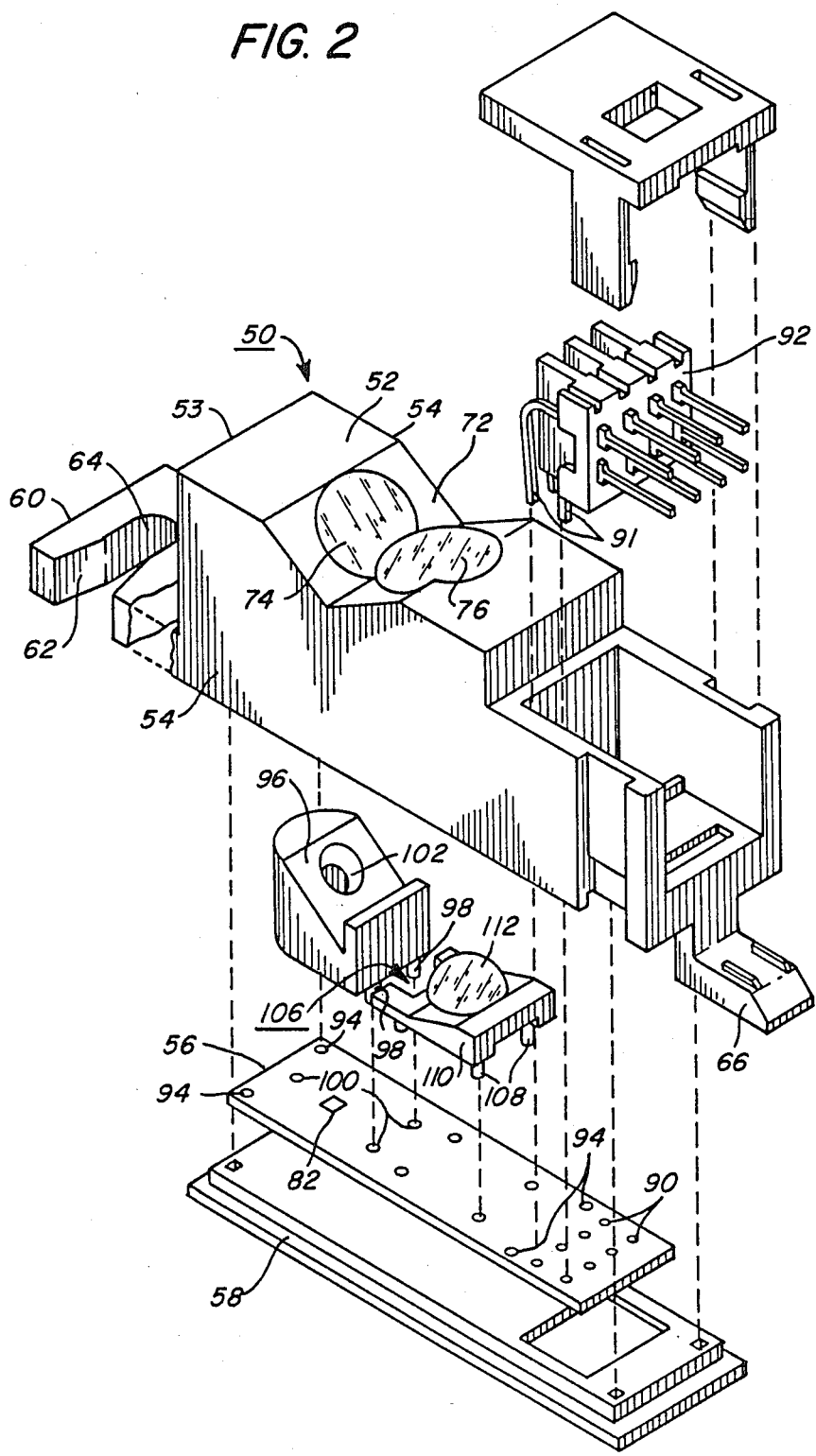
FIG. 2 is an exploded isometric view of an infrared reflectance densitometer made in accord with the present invention.
Figure 3:
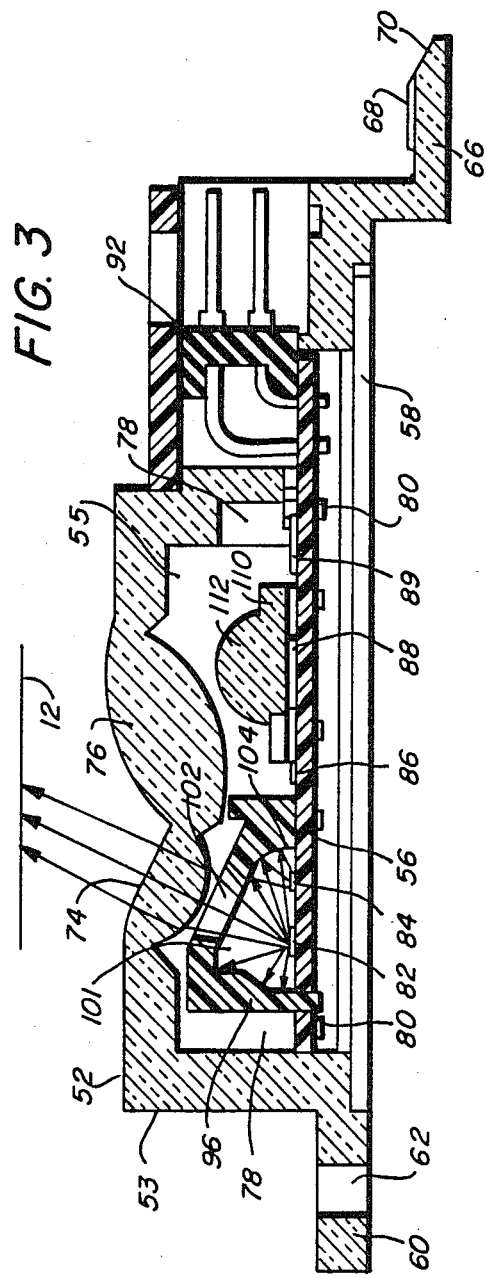
FIG. 3 is an elevational view of the densitometer shown in FIG. 2.

With reference to FIGS. 2 and 3, there is shown an infrared reflectance densitometer comprising a generally rectangular shaped molded housing 50 formed of acrylic or other suitable optically transparent material and having a top wall 52, an end wall 53 and a pair of parallel, spaced side walls 54 enclosing a hollow interior or cavity 55. A substrate 56 formed of a dielectric material such as alumina or conventional printed wireboard provides the bottom wall of the cavity 55 and a cover 58 completes the assembly. Extending from the end wall 53 is an appendage 60 having an elongated slot 62 terminating in a semicircular portion 64. At the distal end of the housing opposite the end wall is an L-shaped tongue 66 integral with the housing and extending away from the substrate. Supported on the L-shaped tongue 66 are a pair of elongated, generally parallel spaced ribs 68 terminating adjacent a beveled surface 70.

The top wall 52 of the rectangular housing 50 defines a V-shaped recession, generally indicated at 72, one surface of the V-shaped recession 72 supporting an integral collimating lens 74 and the other surface of the V-shaped recession 72 supporting an integral collector lens 76. Within the rectangular housing are disposed a plurality of integral abuttments 78, the abuttments being integral with the side walls of the cavity and supporting extending pins 80.

The rectangular substrate 56 forming the bottom wall of the housing supports a suitable light emitting diode (LED) 82 for providing a light signal and also three photodiodes, the first photodiode 84 being a correcting photodiode to collect a portion of the LED radiant flux to compare with a reference in the signal processing circuit to compensate for LED aging and thermal effects. The second photodiode 86 measures various background light in the sensing cavity such as the stray light reflected from the various plastic components, and the third photodiode 88 measures the reflected signal from the photoreceptor surface 12 plus a quantity of undesirable background or stray light. An integrated circuit chip 89 is electrically connected to the LED 82 and diodes 84, 86 and 88 to provide drive current to LED 82 and to process signals from diodes 84, 86 and 88. In operation, the light received by the second photodiode 86 measuring only the background and stray light within the housing is subtracted by the integrated circuit chip 89 from the third photodiode 88 signal providing the signal representing both the background and stray light and the signal reflected from the photoreceptor to give a signal representative of only the reflected signal from the photoreceptor.

Also with reference to FIGS. 2 and 3, disposed in the substrate are a plurality of apertures 90 for receiving the connector leads 91 from a suitable connector 92 as well as a pair of spaced aligned pin holes 94 for receiving the extending pins 80 on the abuttments 78 in the rectangular housing. The engagement of the extending pins 80 in the housing with the pin holes 94 in the substrate 56 connects the substrate to the housing as well as aligns the LED 82 and photodiodes 84, 86, 88 on the substrate 56 with the collimating and collector lenses 74, 76 in the top surface of the housing.

The LED 82 and the photodiodes 84, 86, 88 are suitably bonded to the substrate and the LED 82 first is precisely located on the substrate 56 for proper communication with the various optical elements of the detector. Of critical importance is the alignment of the LED 82 on the substrate 56 with respect to the pin holes 94.

Once the LED 82 is securely aligned with respect to the pin holes 94, the engagement of the pin holes 94 and the extending pins 80 will properly align the LED with the collimating and collector lenses 74 and 76. The square pins 80 are pressed into the round pin holes 94 to rigidly secure the substrate to the housing and fix the relative position of the elements on the substrate with respect to the housing 50.

In addition, an aperture box 96 is fastened to the substrate 56, enveloping the LED 82 and the first photodiode 84. Preferably, the aperture box is molded opaque plastic and includes downwardly extending posts 98 inserted into post holes 100 in the substrate 56 to align and secure the aperture box 96 with respect to the substrate. Extending through the aperture box 96 is a circular aperture 102 communicating with an open space 101 surrounding the LED 82 and the compensation photodiode 84. A portion of the open space 101 is defined by an elliptically shaped surface 104 immediately above the compensation photodiode 84, which is preferably located at one of the focal points of the surface 104. Also mounted on the substrate 56 intermediate the aperture box 96 and the connector 92 is a field lens 106, preferably a molded clear plastic element having pins 108 to secure the field lens 106 to the substrate 56. Essentially, the field lens 106 comprises a platform portion 110 with the pins 108 extending therefrom and a hemispherically shaped lens 112.

In operation, light rays emitted from the LED 82 are either emitted through the aperture 102 of the aperture box 96 through the collimating lens 74 at the surface of the housing, are reflected from the elliptical surface 104 of the aperture box 96 and focused onto the compensation photodiode, or strike the surface of the aperture box 96 opposite the elliptical surface 104 and are dissipated. The elliptical surface 104 serves to focus the internally reflected light rays onto the compensation photodiode 84 and thereby provide an accurate measurement of the intensity of the light output from the LED 82.

The signal generated by the compensation photodiode 84 is conveyed in a feedback loop to suitable control circuitry in integrated circuit chip 89 to drive the LED 82 to provide a relatively constant light output. This compensates for aging of the LED 82, ambient fluctuation, dirt on the lenses, or any other system degradation to maintain a relatively constant light output from the LED 82.

The light rays received by the collimating lens 74 are collimated and directed to the surface of the photoreceptor 12 where they are reflected from the photoreceptor surface 12 in the direction of the collecting or receiving lens 76. The collecting lens 76 gathers the light rays and directs the rays onto the field lens 106 in turn focusing the reflected light onto the signal photodiode 88. The amount of light received at the signal photodiode 88 is a measure of the reflectance of the surface of the photoreceptor surface 12 which is in turn a measure of the degree of toner on the surface 12 of the photoreceptor.

Figure 4:
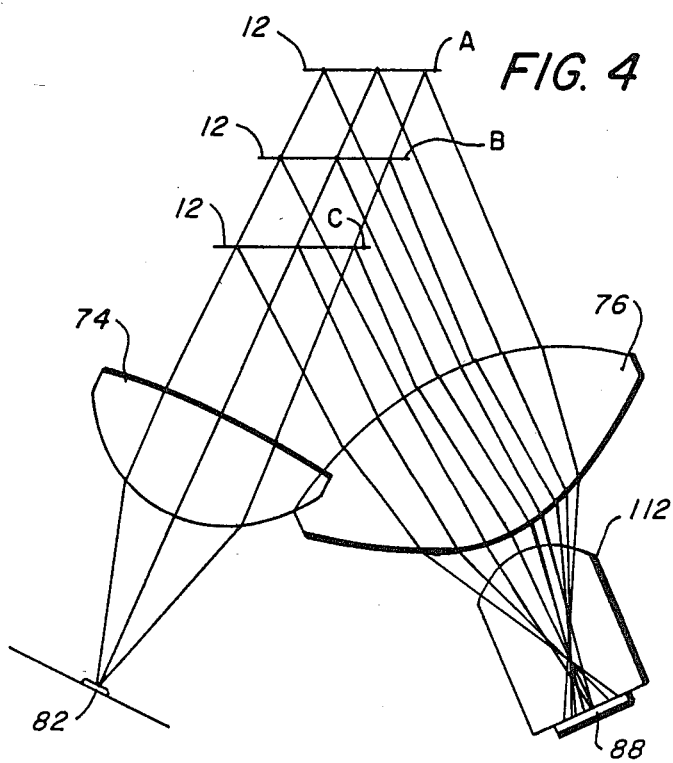
FIG. 4 illustrates lens/photoreceptor relationships for photoreceptor rotation.

In accordance with the present invention, the relationship of the collimating, collecting and field lenses 74, 76, 106 provides accurate detector measurements regardless of the rotation or translation of the photoreceptor surface 12. With respect to FIG. 4, there are shown three respective positions of the photoreceptor web or surface 12 that would normally occur during the movement of the web during operation. This is caused by the tendency of a web type photoreceptor surface to oscillate during movement. In either position A, B or C, the collimating lens 74 projects the light rays from LED 82 onto the web surface 12. At each position A, B or C the light rays are reflected from the surface 12 onto the collecting lens 76 projecting the rays onto the field lens 112 in turn focusing the rays onto the signal photodiode 88. Because of the combination of the lenses 74, 76, 106, there is no loss of reflected light rays on the signal diode due to the translation of the web during operation.

Figure 5:
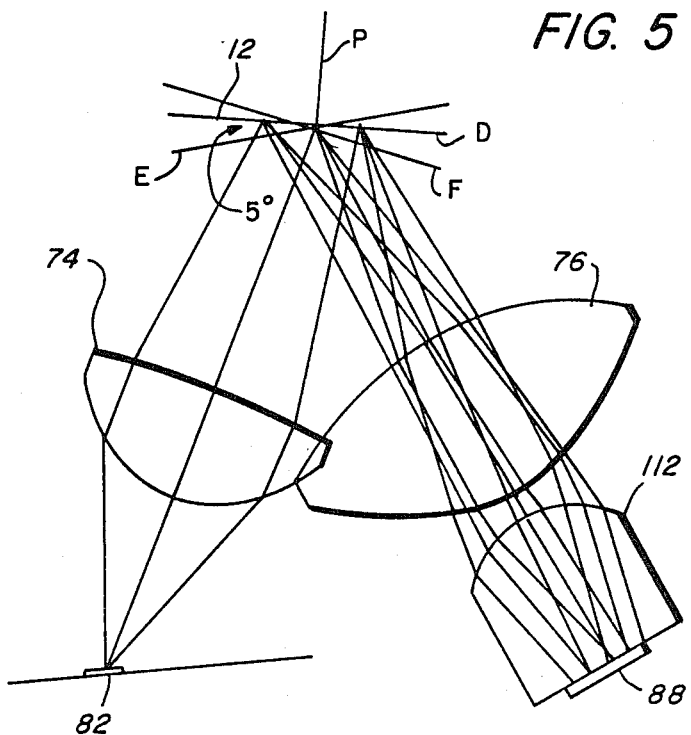
FIG. 5 illustrates lens/photoreceptor relationships for photoreceptor translation.

In a similar manner, there is no loss of light rays reflected from surface 12 due to the rotation of surface 12. With reference to FIG. 5, the light waves from the LED 82 are projected onto the surface 12 of the photoreceptor web. In a first position D, the surface 12 is shown in its normal position, which is 25° to the optical axis of the collimated light beam. In a second position E, the surface 12 has rotated approximately 5° from the direction of the original web position. In position F, the surface 12 has rotated approximately −5° from the direction of the original web position. In any case, the reflected rays from the web surface 12 are gathered by the collector lens 76, projected onto the field lens 112 and focused onto the signal photodiode 88 with no loss of reflected light.

Figure 6:
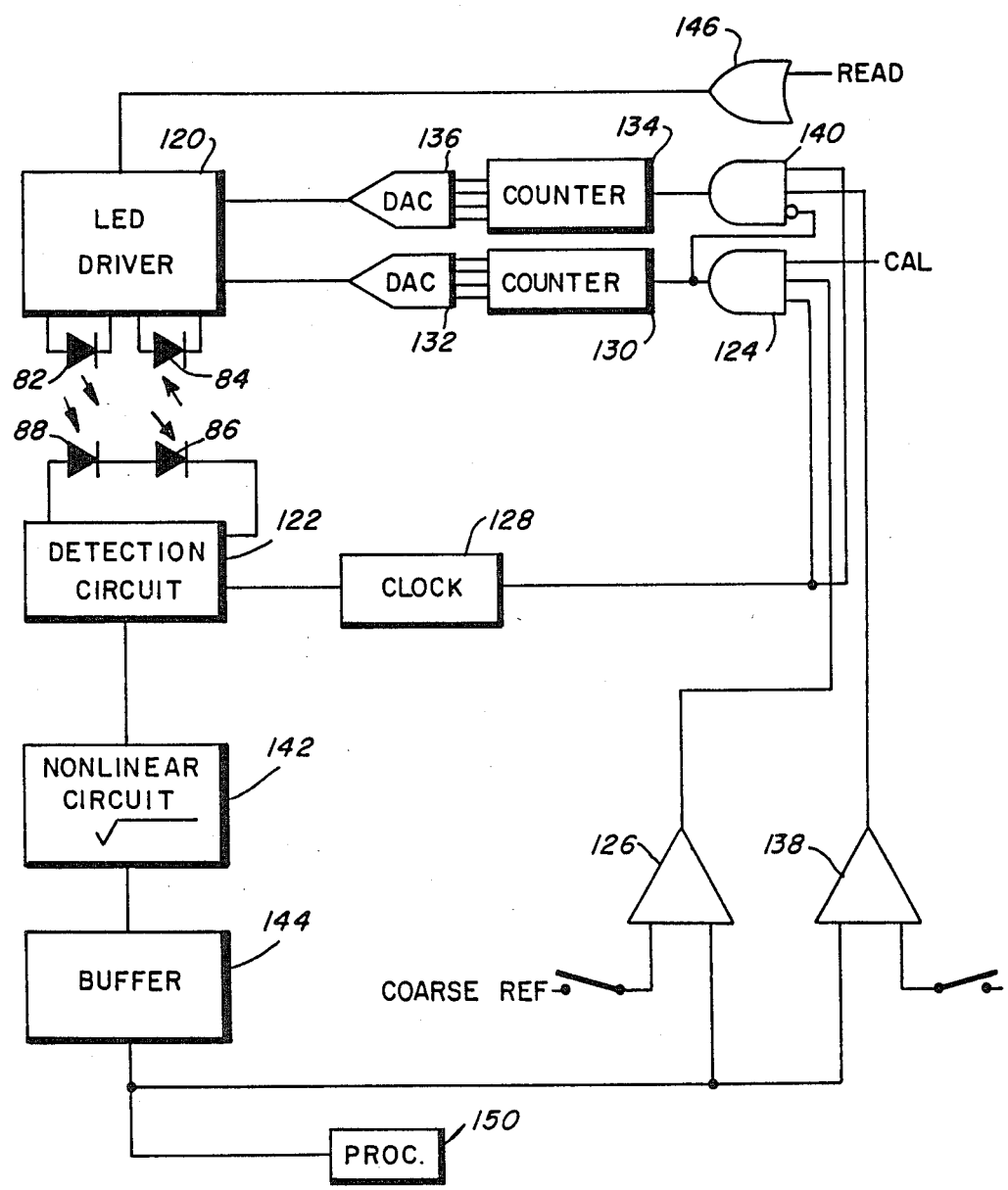
FIG. 6 is a block diagram of the control logic in accordance with the present invention.

With reference to FIG. 6, in accordance with the present invention there is shown a block diagram of the control circuitry in the integrated circuit chip 89 for the infrared densitometer 30. In particular, there is an LED driver circuit 120 for powering the LED 82, a detection circuit 122 for providing a signal representative of the toner concentration on a portion of the surface 12. In operation, the infrared densitometer 30 is at first presented with a clean photoreceptor signal. Initially, an AND gate 124 is enabled by a calibrate signal, CAL, the AND gate also receiving signals from a coarse reference source gate 126 and a clock circuit 128. The coarse reference voltage is approximately 7.5 for a 0 to 10 volt system.

The output of the AND gate 124 is conveyed to a coarse adjust counter in turn connected to a digital to analog converter 132. The output of the converter 132 is conveyed to the LED driver 120. During the calibration cycle, the LED 82 current is first set to the lowest level, about 1 milli amp and the coarse adjust counter 130 and digital to analog converter 132 progressively increase the current by relatively large increments until the output of the digital to analog converter 132 exceeds the coarse reference voltage of 7.5 volts.

When the output of the digital to analog converter 132 exceeds the coarse reference, the coarse counter 130 is disabled and the fine counter 134 enabled. The fine counter 134 is connected to a full scale reference voltage of approximately 9 volts for a 0 to 10 volt system from gate 138 through AND gate 140. The fine counter 134 will increment the LED current in small increments until the output of the digital to analog converter 136 connected to the fine counter 134 exceeds the full scale reference. At this point, the fine counter 134 is stopped and the clean photoreceptor signal will be approximately the desired full scale, approximately 9.0 volts for a 0 to 10 volt system. This level will be held fixed until the next calibration cycle.

Figure 7:
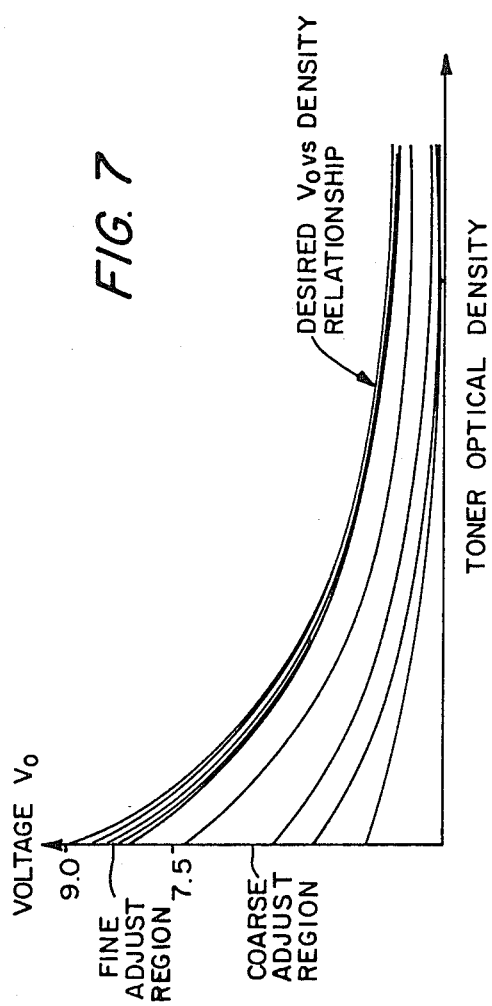
FIG. 7 is a chart illustrating the coarse and fine adjust of the control of FIG. 6.

With reference to FIG. 7, there is shown voltage level as a function of the density of toner. As illustrated, there is a coarse adjustment up to a level of 7.5 volts using the coarse adjust counter 130 with the associated digital to analog converter 132. Then there is the fine adjust in smaller increments to raise the voltage from 7.5 volts to 9.0 volts. The system will then be calibrated to a 9.0 volt curve regardless of the degradation of the detector components.

In operation, with reference to FIGS. 3 and 6, the output of the digital to analog converters 132, 136 control the output of the LED driver 120 in turn producing light rays reflected from the photoreceptor surface 12. The reflected light rays are received by the signal photodetector 88, the LED control photodetector 84, and the control photodetector 86 illustrated in the figure as opposing diode signals. The function of the LED control photodetector 84 is to monitor light rays reflected from elliptical surface 104 of aperture box 96 to feed back signals to LED 82 to compensate for system degradation. The function of the background BG control photodetector 86 is to measure the stray light rays or background light within the system.

The detection circuit 122 subtracts the background signal measured by the background photodetector 86 from the output of the signal diode, thereby providing a detector signal representative of only the light reflected from the photodetector surface 12, in turn representing toner density. This signal is conveyed through a nonlinear circuit 142 and buffer 144 and fed to the machine control or microprocessor 150. The signal is also fed back to the fine and coarse counters 130, 134 through gates 126, 138 during the calibration cycle.

During the read cycle, the densitometer 30 is presented with a reflected signal from a toned test patch. The read gate 146 which is synchronized to the dedicated portion of the surface 12 is then enabled and after a suitable delay, the LED 82 is energized to the light level determined during calibration.

While there has been illustrated and described what is at present considered to be a preferred embodiment of the present invention, it will be appreciated that numerous changes and modifications are likely to occur to those skilled in the art, and it is intended in the appended claims to cover all those changes and modifications which fall within the true spirit and scope of the present invention.

What is claimed is:

1. An infrared densitometer for measuring the relative reflectance of a specularly reflecting surface of a photosensitive web manifesting degrees of translation during measurement including:
    a collimating lens,
    a light source positioned to project light rays through the collimating lens,
    means for measuring and controlling the intensity of light from said source, said means comprising a control photodetector disposed near the light source,
    an aperture box, the aperture box enveloping the light source and the control photodetector and having an elliptical surface, the elliptical surface positioned to focus a portion of the light rays projected from the light source onto the control photodetector,
    a collector lens positioned to receive light rays reflected from the surface of said web,
    a signal photodetector,
    a field lens, the field lens positioned to focus the light rays received from the collector lens onto the signal photodetector, the collector lens and field lens positioned to project a relatively constant amount of light rays reflected from the surface of said web onto the signal photodetector such that signal photodetector signals are independent of the translation of said surface of said web.

2. The densitometer of claim 1 including a background control photodetector, said background control photodetector being disposed external to the aperture box, the background photodetector positioned to receive stray light rays projected from the light source.

3. The densitometer of claim 2 including internal control circuitry electrically connected to the signal photodetector, the background control photodetector and means for subtracting the background control photodetector signal from the signal photodetector signal to provide a densitometer signal representative of the amount of light reflecting from the specularly reflected surface.

4. The densitometer of claim 3 wherein the control circuitry includes a detection circuit, a buffer means positioned to provide the signal representative of the amount of light reflected from the surface, and
    a machine microprocessor, the output of the buffer means being conveyed to the machine microprocessor.

5. The densitometer of claim 3 wherein the control circuitry is an integrated circuit chip.

6. An infrared densitometer comprising
    a substrate having alignment apertures,
    an LED and signal photodetector supported on the substrate, the signal photodetector positioned to receive light rays projected by the LED and reflected by a reflecting surface,
    a field lens secured to the substrate and overlying the signal photodetector,
    an elongated rectangular housing having a pair of essentially parallel side walls and a top surface connected to the side walls,
    a collimating lens and a collector lens integrally molded to the top surface,
    an abuttment extending from the top surface, an aperture box supported on the substrate, the aperture box enveloping the LED and including a hole positioned to direct light rays onto the appropriate portion of the collimating lens, and
    at least two spaced mounting pins projecting from the abuttment, the pins positioned to engage the apertures to align and secure the substrate with the housing, the lenses being positioned such that light is projected from the collimating lens to a reflecting surface, the reflected rays are received by the collector lens and projected onto the field lens and focused onto the signal photodetector.

7. The infrared densitometer of claim 6 including an LED control photodetector supported on the substrate and disposed within the aperture box, the aperture box including an elliptical surface positioned to focus a portion of the light rays projected from the LED onto the control photodetector.

8. The infrared densitometer of claim 7 including a background photodetector supported on the substrate external to the aperture box and immediate the aperture box and the field lens and positioned to provide an indication of background light within the housing.

9. The infrared densitometer of claim 8 including control circuitry and means for subtracting the signal provided by the background photodetector from the signal provided by the signal photodetector, said means comprising a detector circuit to provide a signal indicative of the amount of light reflected from the reflecting surface.

10. The infrared densitometer of claim 6 wherein one end of the elongated housing includes a molded appendage having an elongated aperture with a circular end, the aperture engaging an alignment pin.

11. The infrared densitometer of claim 10 includes a prong, the prong extending from the end of the housing opposite the end of the appendage, the prong including a beveled surface and a pair of spaced essentially parallel elongated ridges.

* * * * *